United States Patent [19]

Saber

[11] Patent Number: 5,308,860
[45] Date of Patent: May 3, 1994

[54] CYANOSULFONYLETHYLTRIAZOLES

[75] Inventor: Steven H. Saber, Horsham, Pa.

[73] Assignee: Rohm and Haas Company, Philadelphia, Pa.

[21] Appl. No.: 6,015

[22] Filed: Jan. 15, 1993

[51] Int. Cl.$^5$ .................. A01N 43/653; C07D 249/08
[52] U.S. Cl. .................. 514/313; 548/267.4
[58] Field of Search .................. 548/267.4; 514/383

[56] References Cited

U.S. PATENT DOCUMENTS

| | | | |
|---|---|---|---|
| 4,366,165 | 12/1982 | Miller et al. | 514/383 |
| 4,675,316 | 6/1987 | Chan | 514/184 |
| 5,087,635 | 2/1992 | Shaber | 514/383 |

Primary Examiner—Patricia L. Morris
Attorney, Agent, or Firm—Clark R. Carpenter

[57] ABSTRACT

This invention relates to substituted 1-((2-cyano-2-(substituted sulfonyl)ethyl)-1,2,4-triazoles of formula (I)

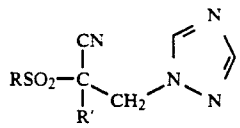

wherein R and R' are each independently alkyl or alkyl substituted with halo, alkoxy or haloalkoxy; aryl or aralkyl, both of which may be substituted on the aryl portion of the moiety with one or more substitutents each independently selected from halo, alkyl, haloalkyl, alkoxy, haloalkoxy, dialkylamino, phenyl, phenoxy, or phenyl or phenoxy substituted with one or two substituents each independently selected from halo and alkyl; heterocyclyl or heterocyclylalkyl, both of which may be substituted on the heterocyclyl ring with one or two substituents each independently selected from halo and alkyl; and their salts, enantiomorphs and metal salt complexes.

7 Claims, No Drawings

CYANOSULFONYLETHYLTRIAZOLES

BACKGROUND OF THE INVENTION

1. Field of the Invention

This invention relates to cyanosulfonylethyltriazoles and their agronomically acceptable enantiomorphs, acid salts and metal salt complexes. This invention also relates to the method of preparation of these compounds and their use as fungicides.

2. Summary of the Background Art

U.S. Pat. No. 4,366,165 and 5,087,635 describe cyanotriazolyl fungicidal compounds.

SUMMARY OF THE INVENTION

The invention relates to cyanosulfonylethyltriazoles, compositions thereof and their use as fungicides.

DETAILED DESCRIPTION OF THE INVENTION

This invention relates to substituted 1-((2-cyano-2-(substituted sulfonyl)ethyl)-1,2,4-triazoles, the agronomically acceptable enantiomorphs, acid addition salts and metal salt complexes thereof and their use as fungicides.

In particular this invention relates to compounds of the formula

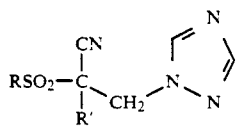

(I)

wherein R and R' are each independently $(C_1-C_{12})$alkyl or $(C_1-C_{12})$alkyl substituted with halo, $(C_1-C_6)$alkoxy or halo$(C_1-C_6)$alkoxy; $(C_6-C_{10})$aryl or $(C_6-C_{10})$ar($C_1-C_6$)alkyl, both of which may be substituted on the aryl portion of the moiety with one or more substituents each independently selected from halo, $(C_1-C_6)$alkyl, halo$(C_1-C_6)$alkyl, $(C_1-C_6)$alkoxy, halo$(C_1-C_6)$alkoxy, di$(C_1-C_6)$alkylamino, phenyl, phenoxy, or phenyl or phenoxy substituted with one or two substituents each independently selected from halo and $(C_1-C_4)$alkyl; heterocyclyl or heterocyclyl$(C_1-C_6)$alkyl, both of which may be substituted on the heterocyclyl ring with one or two substituents each independently selected from halo and $(C_1-C_4)$alkyl; and their salts, enantiomorphs and metal salt complexes.

The term "aryl" means an aromatic ring structure of from 6 to 10 carbon atoms, preferably phenyl or naphthyl, which may be substituted with up to 3 substituents, preferably with up to 2 substituents. Typical aryl and substituted aryl substituents encompassed in this invention are phenyl, naphthyl, 4-chlorophenyl, 4-fluorophenyl, 2,4-dibromophenyl, 2,4-dichlorophenyl, 3,5-difluorophenyl, 2,4,6-trichlorophenyl, 2,3,5-tribromophenyl, 3,4-dichlorophenyl, 2-chloro-4-iodophenyl, 4-methylphenyl, 3,4,5-trimethylphenyl, 4-methoxyphenyl, 2-chloronaphthyl, 2-methylnaphthyl, 2,4-dimethoxyphenyl, 4-(trifluoromethyl)phenyl, 4-(trifluoromethoxy)phenyl, 2,4-diiodonaphthyl, 2-iodo-4-methylphenyl, 4-(dimethylamino)phenyl, 4-(4-chlorophenyl)phenyl, 4-(4-methylphenoxy)phenyl and the like.

The term "heterocyclyl" means 5 and 6 membered unsaturated rings having up to three embedded atoms selected independently from nitrogen, oxygen and sulfur and includes, but is not limited to, 2-pyridyl, 2-thienyl, 4-methyl-2-pyridyl, 4-chloro-2-thienyl, 2-furyl, 2-pyrazinyl, 4-pyrimidinyl and the like.

The term "alkyl" includes both branched and straight chained alkyl of from 1 to 12 carbon atoms such as methyl, ethyl, n-propyl, isopropyl, n-butyl, sec-butyl, isobutyl, tert-butyl, n-pentyl, neopentyl, isopentyl, hexyl, heptyl, iso-octyl, nonyl, decyl, isodecyl, undecyl and dodecyl.

The term "aralkyl" means a $(C_1-C_6)$alkyl group substituted with a $(C_6-C_{10})$aryl group. Typical aralkyl substituents of this invention include benzyl, 4-chlorobenzyl, phenethyl, 4-chlorophenethyl, 4-fluorophenethyl, 4-(trifluoromethyl)phenethyl and the like.

The term "heterocyclyalkyl" means a $(C_1-C_6)$alkyl group substituted with a heterocyclyl group as defined above. Typical heterocyclylalkyl substituents of this invention include 2-pyridylmethyl, furfuryl, 2-thenyl and the like.

The term "alkoxy" includes $(C_1-C_{12})$ straight and branched chain as well as cyclic alkyl groups attached to an oxygen atom such as methoxy, ethoxy, t-butoxy and the like.

The term "halo" includes fluoro, chloro, bromo and iodo.

"Haloalkyl" is, for example, halo$(C_1-C_6)$alkyl such as trifluoromethyl, 2,2,2-trifluoroethyl, chloromethyl, 2-bromoethyl, 3-chloropropyl, 1,3-difluoro-2-propyl and the like.

"Haloalkoxy" is, for example, halo$(C_1-C_6)$alkoxy such as difluoromethoxy, chloromethoxy, 1,3-dichloropropoxy and the like.

"Dialkylamino" is, for example, di$(C_1-C_4)$alkylamino such as dimethylamino, di-n-propylamino and the like.

The acids which can be utilized in making the acid addition salts of the present invention include, for example, hydrochloric, hydrobromic, nitric, sulfuric, phosphoric, hydriodic, hydrofluoric, perchloric, p-toluenesulfonic, methanesulfonic, acetic, citric, tartaric, malic, maleic, oxalic, fumaric, phthalic and the like.

Another embodiment of this invention is the metal salt complex of the formula

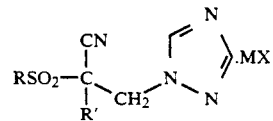

(II)

wherein R and R' are defined in formula I above, M is a cation selected from Group IIA, IVA, IB, IIB, VIB, VIIB or VIII of the Periodic Table and X is an anion counterion selected in such a manner that the sum of the valence charges of the cation M and anion X is 0.

Typical cations encompassed by this invention are magnesium, manganese, copper, nickel, zinc, iron, cobalt, calcium, tin, cadmium, mercury, chromium, lead, barium and the like.

Typical anions encompassed by this invention are chloride, bromide, iodide, fluoride, sulfate, bisulfate, perchlorate, nitrate, nitrite, phosphate, carbonate, bicarbonate, acetate, citrate, oxalate, tartarate, malate, maleate, fumarate, p-toluenesulfonate, methanesulfonate, mono- or di$(C_1-C_4)$alkyldithiocarbamate, $(C_1-C_4)$alkylenebisdithio-carbamate and the like.

A preferred embodiment of this invention is the compounds, agronomically acceptable enantiomorphs, salts and complexes of formulas (I) and (II) wherein R is (C$_1$-C$_6$)alkyl, naphthyl, pyridyl, thienyl, phenyl or phenyl substituted with up to two substituents each independently selected from halo, (C$_1$-C$_4$)alkyl, halo(C$_1$-C$_4$)alkyl, (C$_1$-C$_4$)alkoxy and halo(C$_1$-C$_4$)alkoxy; and R' is (C$_1$-C$_6$)alkyl, pyridyl, phen(C$_1$-C$_4$)alkyl or phen(C$_1$-C$_4$)alkyl substituted on the phenyl ring with up to two substituents each independently selected from halo, (C$_1$-C$_4$)alkyl, halo(C$_1$-C$_4$)alkyl, (C$_1$-C$_4$)alkoxy and halo(C$_1$-C$_4$)alkoxy.

A more preferred embodiment of this invention is the compounds, agronomically acceptable enantiomorphs, salts and complexes of formulas (I) and (II) wherein R is phenyl, 4-chlorophenyl, 2,4-dichlorophenyl, 4-methylphenyl, 2-pyridyl, 2-naphthyl, 2-thienyl, n-propyl, isopropyl, n-butyl, n-pentyl, n-hexyl or t-butyl and R' is n-propyl, n-butyl, n-pentyl, isopentyl, benzyl, 4-chlorobenzyl, phenethyl, 4-chlorophenethyl, 4-fluorophenethyl, 4-methylphenethyl, 4-(trifluoromethyl)-phenethyl or 2-pyridyl.

An even more preferred embodiment of this invention is the compounds, agronomically acceptable enantiomorphs, salts and complexes of formulas (I) and (II) wherein R is t-butyl, phenyl, 4-chlorophenyl, 2,4-dichlorophenyl or 4-methylphenyl and R' is n-propyl, n-butyl, 4-chlorobenzyl, phenethyl, 4-chlorophenethyl or 4-fluorophenethyl.

The substituted 1-((2-cyano-2-(substituted sulfonyl)ethyl)-1,2,4-triazoles of this invention can be prepared by standard synthetic routes. There are two preferred methods for preparing the compounds of this invention as indicated below:

METHODS OF PREPARATION

RSO$_2$CH$_2$CN + R'Z  Route A
(1a)
⟶ RSO$_2$CHR'CN
(2)
RSO$_2$Cl + R'CH$_2$CN  Route B
(1b)

2 step sequence

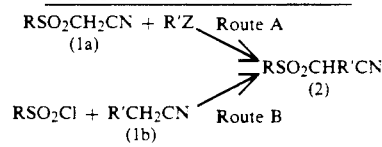

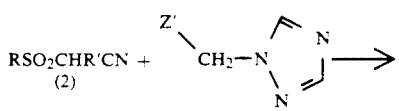

3 step sequence

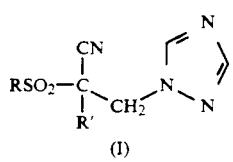

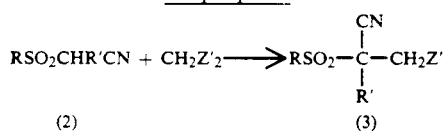

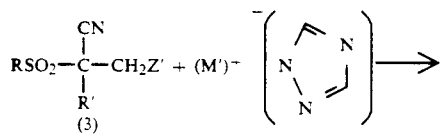

-continued
METHODS OF PREPARATION

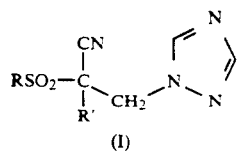

Route A is employed when R' is other than aryl or heterocyclyl. A sulfonyl acetonitrile derivative (1a) is alkylated with R'Z under basic conditions to provide the alkylated intermediate (2) wherein R and R' are as defined in formula (I), except that R' is not aryl or heterocyclyl, and Z is a chloride, bromide, iodide, methylsulfonate, phenylsulfonate, 4-tolylsulfonate or any other leaving group capable of effecting the desired reaction. Route B is preferred when R' is aryl or heterocyclyl. An aryl or heterocyclyl acetonitrile (1b) is sulfonylated with RSO$_2$Cl under basic conditions to provide the intermediate (2) wherein R and R' are as defined in formula (I). For both Routes A and B, the temperatures employed are from about −20° C. to about 100° C., preferably from about −10° C. to about 60° C., and more preferably from about 20° C. to about 50° C. Examples of suitable bases include a hydride or a hydroxide of a Group IA metal, preferably sodium or potassium. Dimethyl sulfoxide (DMSO), is a particularly advantageous solvent for use with hydroxides while N,N-dimethylformamide (DMF) is a preferred solvent for use with hydrides. An alternative procedure to prepare the sulfonylated acetonitrile intermediate (2) employs phase transfer conditions in the presence of a base, such as a hydroxide, a solvent such as methylene chloride, chloroform, carbon tetrachloride, benzene, toluene, ethers, tetrahydrofuran (THF) and dioxane. The phase transfer conditions usually require catalysts, examples of which include tetrabutylammonium hydroxide, tetrabutylammonium bromide, benzyltriethylammonium chloride or other quaternary ammonium salts, quaternary phosphonium salts and crown ethers, for example, 18-crown-6.

The alkylated intermediate of formula (2) can be treated under basic conditions with a halomethyltriazole, wherein Z' is chloro or bromo, to provide the compounds of the invention as shown by formula (I). Alternatively, the alkylated intermediate of formula (2) can be treated in a two step sequence, the first step being reaction with a dihalomethane, wherein Z' is chloro or bromo, to form the halomethyl intermediate of formula (3) and the second step being reaction of the intermediate of formula (3) with a triazole salt wherein (M')$^+$ is a sodium or a potassium cation or a mixture of sodium and potassium cations. Similar sequences are provided in U.S. Pat. No. 4,366,165 and U.S. Pat. No. 5,087,635, the disclosures of which are incorporated by reference herein.

The acid addition salts of the compounds of this invention can be prepared by standard known techniques. For example, the compounds of formula (I) can be dissolved in an appropriate solvent such as diethyl ether, tetrahydrofuran, ethanol, methanol, and the like or combinations thereof, and treated with an equivalent or excess amount of a mineral or organic acid which may or may not be dissolved in an appropriate solvent. The mixture is then either cooled or evaporated to yield the salt which can either be used as such or recrystallized from an appropriate solvent or combination of appropriate solvents.

The metal salt complexes of formula (II) can be prepared by adding dropwise, with stirring, a stoichiometric amount of a metal salt dissolved in an appropriate solvent or combination of solvents to a solution of the compounds of formula (I) dissolved in a similarly appropriate solvent of combination of solvents. The reaction mixture is briefly stirred and the solvent is removed under reduced pressure to give the metal salt complex of the respective compounds of formula (II).

The metal salt complexes can also be prepared by mixing stoichiometric or excess amounts of the metal salt and a compound of formula (I) in the desired amount of solvent containing the appropriate adjuvants just prior to spraying the plants. Adjuvants that may be included in this "in situ" preparation may be detergents, emulsifiers, wetting agents, spreading agents, dispersing agents, stickers, adhesives, and the like which are used in agricultural applications.

Solvents that can be utilized in these procedures include any polar solvent, for example, water, methanol, ethanol, isopropanol or ethylene glycol and any aprotic dipolar solvent, for example, dimethylsulfoxide, acetonitrile, dimethylformamide, nitromethane or acetone.

The metal salt cations that can be used in these procedures can be selected from the group consisting of calcium, magnesium, manganese, copper, nickel, zinc, iron, cobalt, tin, cadmium, mercury, chromium, lead, barium and the like.

Any appropriate anion, for example, chloride, bromide, iodide, sulfate, bisulfate, phosphate, nitrate, perchlorate, carbonate, bicarbonate, hydrosulfide, hydroxide, acetate, oxalate, malate, citrate and the like may be utilized as the counterion in the metal salt.

Many metal containing fungicides can also act as safening agents when used in place of metal salts. Typical metal containing fungicides that can be utilized in these procedures are: (a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb); (b) copper-based fungicides such as cuprous oxide, copper oxychloride, copper naphthenate, and Bordeaux mixture; and (c) miscellaneous fungicides such as: phenylmercuric acetate, N-ethylmercuri-1,2,3,6-tetrahydro-3,6-endomethano-3,4,5,6,7,7-hexachlorophthalimide, phenylmercuri monoethanolammonium lactate, nickel-containing compounds and calcium cyanamide.

The compounds of this invention possess an asymmetric carbon atom and thus exist as racemic mixtures. The d and l enantiomorphs in these racemic mixtures can be separated via standard techniques such as fractional crystallization with d-tartaric acid, l-tartaric acid, l-quinic acid and the like followed by basification and extraction of the d or l enantiomorph free base.

COMPOUNDS EMBRACED BY THIS INVENTION

Table 1 lists examples which are provided merely to illustrate the methods of preparation and use of the compounds of the present invention. They are not intended to limit the scope of the invention which is defined by the claims.

TABLE 1

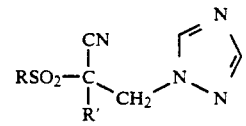

| Example | R | R' |
|---|---|---|
| 1 | t-butyl | 4-chlorophenethyl |
| 2 | phenyl | 4-chlorophenethyl |
| 3 | phenyl | n-butyl |
| 4 | 4-chlorophenethyl | n-butyl |
| 5 | 2,4-dichlorophenyl | n-butyl |
| 6 | 4-(trifluoromethyl)phenyl | n-propyl |
| 7 | 2-pyridyl | n-propyl |
| 8 | 2-pyridyl | 4-fluorophenethyl |
| 9 | 2-naphthyl | n-butyl |
| 10 | 2-thienyl | 4-chlorophenethyl |
| 11 | n-propyl | 4-(trifluoromethyl)phenethyl |
| 12 | isopropyl | n-pentyl |
| 13 | n-butyl | isopentyl |
| 14 | n-butyl | 4-fluorophenethyl |
| 15 | n-pentyl | 4-chlorobenzyl |
| 16 | n-hexyl | phenethyl |
| 17 | t-butyl | n-butyl |
| 18 | t-butyl | 2-pyridylmethyl |

EXPERIMENTAL

Preparation of Example 1:
4-(4-Chlorophenyl)-2-(t-Butylsulfonyl)-2-((1,2,4-Triazol-1-yl)methyl)butanenitrile Preparation of
4-(4-chlorophenyl)-2-(t-butylsulfonyl)butanenitrile Into a 3-neck, 200 milliliter (mL) round bottom flask was charged 2.4 grams (g), 0.06 mole, of 60% sodium hydride (NaH), which had been previously washed two times with successive 30 mL portions of hexane, in 30 mL of dimethylformamide (DMF). While stirring under nitrogen, 7.6 g (0.05 mole) of t-butylsulfonylacetonitrile in 25 mL of DMF was added. The mixture was stirred for 0.5 hour (hr) and 12.8 g (0.055 mole) of 2-(4-chlorophenyl)ethyl methanesulfonate in 25 mL of DMF was added dropwise. The mixture was stirred at room temperature for 3 hrs. and then an additional 96 hrs by which time the mixture had changed to an orange slurry. The mixture was stirred yet an additional 96 hrs at room temperature after which analysis by gas liquid phase chromatography (GLC) indicated the absence of starting material. The reaction was quenched by the addition of 100 mL of diethyl ether and 50 mL of water. The ether was washed with water and the combined aqueous phases were extracted with 50 mL of ethyl acetate. The organic phases were combined, dried with sodium sulfate, filtered and concentrated to give 12.0 g of an orange oil (80.3% yield) which was used directly in the next step.

NMR (200 MHz, CDCl$_3$): 1.55 (9H, s), 2.4–2.5 (2H, m), 2.8–2.9 (1H, m), 3.0–3.1 (1H, m), 3.8–3.9 (1H, m) and 7.1–7.5 (4H, m).

Preparation of
4-(4-chlorophenyl)-2-(t-butylsulfonyl)-2-((1,2,4-triazol-1-yl)methyl)butanenitrile Into a 3-neck, 300 mL round bottom flask was charged 2.0 g (0.05 mole, 2.5 equivalents (eq)) of 60% NaH, which had been previously washed two times with successive 30 mL portions of hexane, in 50 mL of DMF. While stirring under nitrogen, 5.98 g (0.020 mole, 1.0 eq) of 4-(4-chlorophenyl)-2-(t-butylsulfonyl)-butanenitrile in 50 mL of DMF was added dropwise over 0.5 hr. The mixture was stirred for an additional 45 minutes after which 1-(chloromethyl)-1,2,4-triazole hydrochloride (3.36 g, 0.022 mole), was added directly in two portions. The mixture was stirred at room temperature for 12 hrs, 40° C. for 8 hrs and 45° C. for 12 hrs after which analysis by GLC indicated the reaction was complete. The reaction was quenched by the addition of water and extracted with 150 mL of ethyl acetate, dried with sodium sulfate, filtered and concentrated to give 10 g of crude product. The product was purified by column chromatography on silica gel. Elution with hexane:ethyl acetate (2:1) gave 3.6 g of an oil (fractions 1-5) which was followed by elution with hexane:ethyl acetate (1:1) to give an additional 1.0 g of oil. Both fractions contained a major and minor product as observed using thin layer chromatography (TLC) in ethyl acetate:hexane (1:1). The 3.6 grams of oil was further purified by flash chromatography on silica gel with hexane:ethyl acetate (1:1). The product was collected in fractions 34-60 (20 mL fractions) and gave 1.4 g of a thick yellow oil.

| Elemental Analysis for $C_{17}H_{21}N_4ClSO_2$: | | | | | |
| --- | --- | --- | --- | --- | --- |
| | C | H | N | Cl | S | O |
| Calc: | 53.61 | 5.52 | 14.72 | 9.33 | 8.41 | 8.41 |
| Found: | 53.90 | 5.51 | 15.01 | 9.43 | 8.16 | 8.64 |

NMR (200 MHz) CDCl$_3$: 1.7 (9H, s), 2.3-2.5 (2H, m), 2.9-3.1 (2H, t), 4.9-5.1 (2H, q), 7.1-7.4 (4H, m), 8.1 (1H, s) and 8.4 (1H, s).

IR (NaCl plate, cm$^{-1}$): 3140 (w), 2240 (w), 1500 (m), 1415 (w), 1380 (w), 1310 (s), 1280 (m), 1215 (m), 1185 (m), 1120 (s), 1040 (m), 960 (m), 920 (m), 820 (m), 750 (m), and 685 (m).

In a similar manner, the compounds of examples 2-18 may be prepared using the procedures described hereinabove.

Fungicidal Data for Example 1

In Vitro Fungicidal Testing

The compound of Example 1 was tested in a microtiter plate assay for fungicidal activity against a variety of fungi at a 25 parts per million (ppm) dosage rate.

The following organisms were employed in the test: *Botrytis cinerea* (BOC), *Rhizoctonia solani* (RHI), *Cercospora beticola* (CER), *Monilinia fructicola* (MON), and *Pseudocercosporella herpotrichoides* (PSH).

All fungi were transferred and maintained on potato dextrose agar (PDA) plates. To prepare inoculum, RHI was grown in a yeast extract-dextrose broth (YDB). After two days growth the culture was homogenized and diluted into fresh YDB. Inoculum of BOC, MON, CER and PSH were prepared by scraping conidia from the surface of cultures grown on PDA into YDB. The conidial suspensions were strained through a double layer of cheesecloth to remove any mycelial clumps. The various inoculum preparations were added in 175 microliter ($\mu$L) aliquots to wells of 96-well microtiter plates with two replicate wells per treatment. Test compounds were dissolved in acetone/methanol (1:1) at a concentration of 10 milligrams (mg)/mL, then 5 $\mu$L of the solution is added to 245 $\mu$L of sterile water to give 200 ppm solutions. Aliquots (25 $\mu$L) of each solution were added to the inoculum in the microtiter plates to give a concentration of 25 ppm. Microtiter plates were incubated for 3 days at room temperature and fungal growth recorded as % control by comparison with control wells without test compound.

The results (expressed as percent inhibition of fungal growth) of in vitro testing of the compound of example 1 are presented below:

| BOC | RHI | CER | PSH | MON |
| --- | --- | --- | --- | --- |
| 50 | 100 | 90 | 100 | 100 |

In Vivo Fungicidal Testing

The compound of example 1 of this invention was tested for fungicidal activity in vivo against wheat leaf rust (WLR), wheat powdery mildew (WPM), and wheat leaf blotch (SNW). The plants to be tested were trimmed about 24 hours prior to the application of the fungicide compound to provide a uniform plant height and to facilitate uniform application of the compound and inoculation with the fungus. The compounds were dissolved in a 2 to 1 to 1 mixture of water, acetone, and methanol, sprayed onto the plants, allowed to dry, and then the plants were inoculated with the fungus 24 hours after spraying. Each test utilized control plants which were sprayed with the water, acetone, and methanol mixture and inoculated with the fungus. The remainder of the technique for each of the tests is given below. Results are reported as percent disease control (percentage of a plant treated with the compound of example 1 of the present invention lacking disease signs or symptoms compared to an inoculated, untreated control plant).

Wheat Leaf Rust (WLR):

*Puccinia recondita* (f. sp. *tritici* Races PKB and PLD) was cultured on seven day old wheat (cultivar Fielder) over a 14 day period in the greenhouse. Spores were collected from the leaves, cleaned by sieving through a 250 micron opening screen and stored or used fresh. A spore suspension was prepared from dry uredia by adding 20 mg (9.5 million spores) per mL of Soltrol oil. The suspension was dispensed into gelatin capsules (0.7 mL capacity) which attach to the oil atomizers. One capsule was used to inoculate a flat of twenty of the two inch square pots of seven day old Fielder wheat. The plants were placed in a darkmist chamber (18°-20° C. and 100% relative humidity) for 24 hours. The plants were then put in the greenhouse for the latent period and scored after 10 days for disease levels. Protective and curative tests were inoculated one day after and two days, respectively, before spraying the plants with the test chemicals.

Wheat Powdery Mildew (WPM):

*Erysiphe graminis* (f. sp. *tritici*) was cultured on Hart wheat seedlings in a controlled temperature room at 65°-75° F. Mildew spores were shaken from the culture plants onto Hart wheat seedlings which had been sprayed previously with the fungicide compound. The inoculated seedlings were kept in a controlled temperature room at 65°-75° F. and subirrigated. The percent disease control was rated eight days after the inoculation.

Wheat Leaf Blotch (SNW):

*Septoria nodorum* was maintained on Czapek-Dox V-8 Juice agar plates in an incubator in the dark at 20° C. for 48-72 hours, then incubated at 20° C. with alternating periods of 12 hours of light and 12 hours of darkness. A water suspension of the spores, obtained from the plates by shaking the portion of the plate with fungal material in deionized water and filtering through cheesecloth, was diluted to a spore concentration of $3.0 \times 10^6$ per mL. The inoculum was dispersed by a DeVilbiss atomizer over one week old Fielder wheat plants which had been sprayed previously with the fungicide compound. The inoculated plants were placed in a humidity cabinet at 20° C. with alternating periods of 12 hours of light and 12 hours of darkness for 96 hours. The inoculated seedlings were then moved to a controlled environment room as above and scored after 8 more days of incubation. Disease control levels were recorded as percent control 10 days after inoculation.

The results of the tests for the compound of example 1 at a 200 ppm application rate are shown below:

| SNW | WLR | WPM |
|---|---|---|
| 80 | 90 | 75 |

The substituted 1-((2-cyano-2-(substituted sulfonyl)ethyl)-1,2,4-triazoles, their enantiomorphs, acid addition salts and metal salt complexes of the present invention are useful as agricultural fungicides and as such can be applied to various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in the John W. McCutcheon, Inc. publication "Detergents and Emulsifiers, Annual."

In general, the compounds of this invention can be dissolved in certain solvents such as acetone, methanol, ethanol, dimethylformamide, pyridine or dimethyl sulfoxide and such solutions can be extended with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually from about 10% to about 90% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 98%, preferably from about 40% to about 75%. A typical wettable powder is made by blending 50 parts of a cyanosulfonylethyltriazole, 45 parts of a synthetic precipitated hydrated silicon dioxide, and 5 parts of sodium lignosulfonate. In another preparation a kaolin type (Barden) clay is used in place of the Hi-Sil in the above wettable powder, and in another such preparation 25% of the hydrated silicon dioxide is replaced with a synthetic sodium silica aluminate.

Dusts are prepared by mixing the cyanosulfonylethyltriazoles, enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The compounds of this invention, their enantiomorphs, salts and complexes thereof can be applied as fungicidal sprays by methods commonly employed, such as conventional high-gallonage hydraulic sprays, low-gallonage sprays, air-blast sprays, aerial sprays and dusts. The dilution and rate of application will depend upon the type of equipment employed, the method of application and diseases to be controlled, but the preferred effective amount is usually from about 0.1 lb. to 50 lbs. per acre of the active ingredient.

As a seed protectant, the amount of the compounds of this invention coated on the seed is usually at a dosage rate of from about 0.1 to about 20 ounces per hundred pounds of seed. As a soil fungicide the compounds of this invention can be incorporated in the soil or applied to the surface usually at a rate of from about 0.1 to about 50 pounds per acre. As a foliar fungicide, the compounds of this invention are usually applied to growing plants at a rate of from about 0.25 to about 10 pounds per acre.

Fungicides which can be combined with the fungicides of this invention include:

(a) dithiocarbamate and derivatives such as: ferbam, ziram, maneb, mancozeb, zineb, propineb, metham, thiram, the complex of zineb and polyethylene thiuram disulfide, dazomet, and mixtures of these with copper salts;

(b) nitrophenol derivatives such as: dinocap, binapacryl, and 2-sec-butyl-4,6-dinitrophenyl isopropyl carbonate;

(c) heterocyclic structures such as: captan, folpet, glyodine, anilazine, ditalimfos, 4-butyl-1,2,4-triazole, 5-amino-1[bis(dimethylamino)phosphinyl]-3-phenyl-1,2,4-triazole, etradiazole, dithianon, thioquinox, benomyl, thiabendazole, 4-(2-chlorophenylhydrazono)-3-methyl-5-isoxazolone, vinclozolin, iprodione, procymidone, triadimenol, triadimefon, bitertanol, prochloraz, fenarimol, bis-(p-chlorophenyl)-3-pyridinemethanol, bis-(p-chlorophenyl)-5-pyrimidinemethanol, triarimol, flutriafol, flusilazole, propiconazole, ectaconazole, myclobutanil, fenbuconazole, hexaconazole, cyprconazole, tebuconazole, diniconazole, fluoroimide, pyridine-2-thiol-1-oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin, cis-N-[(1,1,2,2-tetrachloroethyl)-thiol]-4-cyclohexene-1,2-dicarboximide, cycloheximide, dehydroacetic acid, captafol, ethirimol, quinomethionate, D,L-methyl-N-(2,6-dimethylphenyl)-N-(2'-methoxyacetyl)alanine methyl ester, D,L-methyl-N-(2,6-dimethylphenyl)-N-chloroacetyl-D,L-2-aminobutyrolactone, D,L-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-(methoxymethyl)-1,3-oxazolidi-2,4-dione, 3-(3,5-dichlorophenyl)-1-isopropylcarbamoylhydantoin, 2-cyano-[N-(ethylaminocarbonyl)-2-methoximino]acetamide, fenpropimorph, fenpropidine, 2,6-dimethyl-N-tridecylmorpholine, dodemorph, and triforine;

(d) miscellaneous halogenated fungicides such as: chloranil, dichlone, chloroneb, tricamba, TCPN, dichloran, 2-chloro-1-nitropropane, polychloronitrobenzenes such as pentachloronitrobenzene (PCN B), and tetrafluorodichloroacetone;

(e) fungicidal antibiotics such as: griseofulvin, kasugamycin, polyoxin, validamycin, and streptomycin;

(f) copper-based fungicides such as: copper hydroxide, cuprous oxide, basic cupric chloride, basic copper carbonate, copper terephthalate, copper naphthenate and Bordeaux mixture; and (g) fungicides such as: dodine, phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzene sodium sulfonate, methyl isothiocyanate, 1-thiocyano-2,4-dinitrobenzene, 1-phenylthiosemicarbazide, nickel-containing compounds, calcium cyanamide, lime sulfur, thiophanate-methyl, flutolanil, edinophos, isoprothiolane, propenazole, and tricyclazole.

The compounds, enantiomorphs, acid addition salts and metal salt complexes of this invention can be advantageously employed in various ways. Since these compounds possess broad spectrum fungicidal activity, they can be employed in the storage of cereal grain. These complexes can also be employed as fungicides in turf, fruit orchards, vegetables and golf course applications. Other applications of the compounds of this invention will suggest themselves to those skilled in the art of agriculture and horticulture.

I claim:

1. A compound of the formula

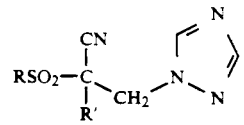

wherein R and R' are each independently $(C_1-C_{12})$alkyl or $(C_1-C_{12})$alkyl substituted with halo, $(C_1-C_6)$alkoxy or halo$(C_1-C_6)$alkoxy; $(C_6-C_{10})$aryl or $(C_6-C_{10})$ar$(C_1-C_6)$alkyl, both of which may be substituted on the aryl portion of the moiety with one or more substituents each independently selected from halo, $(C_1-C_6)$alkyl, halo$(C_1-C_6)$alkyl, $(C_1-C_6)$alkoxy, halo$(C_1-C_6)$alkoxy, di$(C_1-C_6)$alkylamino, phenyl, phenoxy, or phenyl or phenoxy substituted with one or two substituents each independently selected from halo and $(C_1-C_4)$alkyl; or their salts, enantiomorphs and metal salt complexes.

2. The compound of claim 1 wherein R is $(C_1-C_6)$alkyl, naphthyl, phenyl or phenyl substituted with up to two substituents each independently selected from halo, $(C_1-C_4)$alkyl, halo$(C_1-C_4)$alkyl, $(C_1-C_4)$alkoxy and halo$(C_1-C_4)$alkoxy; and R' is $(C_1-C_6)$alkyl, phen$(C_1-C_4)$alkyl or phen$(C_1-C_4)$alkyl substituted on the phenyl ring with up to two substituents each independently selected from halo, $(C_1-C_4)$alkyl, halo$(C_1-C_4)$alkyl, $(C_1-C_4)$alkoxy and halo$(C_1-C_4)$alkoxy.

3. The compound of claim 2 wherein R is phenyl, 4-chlorophenyl, 2,4-dichlorophenyl, 4-methylphenyl, 2-naphthyl, n-propyl, isopropyl, n-butyl, n-pentyl, n-hexyl or t-butyl and R' is n-propyl, n-butyl, n-pentyl, isopentyl, benzyl, 4-chlorobenzyl, phenethyl, 4-chlorophenethyl, 4-fluorophenethyl, 4-methylphenethyl, or 4-(trifluoromethyl)phenethyl.

4. The compound of claim 3 wherein R is t-butyl, phenyl, 4-chlorophenyl, 2,4-dichlorophenyl or 4-methylphenyl and R' is n-propyl, n-butyl, 4-chlorobenzyl, phenethyl, 4-chlorophenethyl or 4-fluorophenethyl.

5. The compound of claim 4 wherein R is t-butyl and R' is 4-chlorophenethyl.

6. A fungicidal composition which comprises an agronomically acceptable carrier and a fungicidally effective amount of a compound of claim 1.

7. A method for controlling fungi which comprises applying to the locus where control is desired a fungicidally effective amount of a compound of claim 1.

* * * * *

UNITED STATES PATENT AND TRADEMARK OFFICE
CERTIFICATE OF CORRECTION

PATENT NO.   :   5,308,860
DATED        :   May 3, 1994
INVENTOR(S)  :   Steven H. Shaber It is certified that error appears in the above-identified patent and that said Letters Patent is hereby corrected as shown below:

On the Title Page, item [75], please change "Steven H. Saber" to --Steven H. Shaber--.

Signed and Sealed this

Twenty-third Day of August, 1994

Attest:

BRUCE LEHMAN

Attesting Officer

Commissioner of Patents and Trademarks